United States Patent
Sartorius et al.

(10) Patent No.: US 8,064,740 B2
(45) Date of Patent: Nov. 22, 2011

(54) ARRANGEMENT FOR THE ELECTRO-OPTICAL CONTROL AND FAST MODULATION OF THZ TRANSMITTERS AND THZ MEASURING SYSTEMS

(75) Inventors: Bernd Sartorius, Berlin (DE); Michael Feiginov, Darmstadt (DE); Cezary Sydlo, Floersheim (DE)

(73) Assignees: Fraunhofer-Gesellschaft zur Foerderung der Angewandten Forschung E.V., Munich (DE); Technische Universitaet Darmstadt, Darmstadt (DE)

(*) Notice: Subject to any disclaimer, the term of this patent is extended or adjusted under 35 U.S.C. 154(b) by 342 days.

(21) Appl. No.: 12/517,732

(22) PCT Filed: Nov. 30, 2007

(86) PCT No.: PCT/EP2007/010411
§ 371 (c)(1),
(2), (4) Date: Jun. 4, 2009

(87) PCT Pub. No.: WO2008/067957
PCT Pub. Date: Jun. 12, 2008

(65) Prior Publication Data
US 2010/0080505 A1    Apr. 1, 2010

(30) Foreign Application Priority Data
Dec. 7, 2006 (DE) .................. 10 2006 058 395

(51) Int. Cl.
*G02B 6/12* (2006.01)

(52) U.S. Cl. ................. 385/14; 385/15; 385/31
(58) Field of Classification Search .......... 385/14, 385/15, 31, 27, 45
See application file for complete search history.

(56) References Cited

U.S. PATENT DOCUMENTS

| | | | |
|---|---|---|---|
| 5,222,162 A | 6/1993 | Yap et al. | |
| 5,280,549 A * | 1/1994 | Barnard et al. | 385/15 |
| 5,710,651 A | 1/1998 | Logan | |
| 5,883,914 A | 3/1999 | Kinoshita | |
| 6,545,785 B1 | 4/2003 | Heflinger et al. | |
| 2005/0259908 A1 | 11/2005 | Donati et al. | |

FOREIGN PATENT DOCUMENTS

| | | |
|---|---|---|
| DE | 692 21 129 | 7/1997 |
| DE | 696 10 675 | 10/2000 |
| WO | 00 36718 | 6/2000 |
| WO | 2006 123163 | 11/2006 |

OTHER PUBLICATIONS

Mendis et al., "Coherent Generation and Detection of Continuous Terahertz Waves Using Two Photomixers Driven by Laser Diodes," *International Journal of Infrared and Millimeter Waves*, vol. 26, No. 2, pp. 201-207, (Feb. 2005).

* cited by examiner

*Primary Examiner* — Ellen Kim
(74) *Attorney, Agent, or Firm* — Greenblum & Bernstein, P.L.C.

(57) ABSTRACT

An inexpensive and compact arrangement for the electrical control and fast modulation of THz transmitters and THz measuring systems is proposed, wherein said arrangement is stable, requires no mechanical movements and operates with a purely electric control, consumes little power and also has a high speed potential for the phase modulation. This is achieved by replacing the components known from the state of the art, namely two lasers, the beam splitters, the couplers and the mechanically moved delay line, with a compact monolithic or hybrid integrated chip (10), particularly a so-called optical master chip without moving parts that comprises at least the two lasers (1, 2), the beam splitters (S3.1, S3.2), the couplers (K3.1, K3.2) and a phase modulator (4.1) for one of the laser waves such that the two generated beat signals are respectively delivered to different chip outputs (6, 7) in order to separately control the THz transmitter and the local oscillator.

18 Claims, 3 Drawing Sheets

ARRANGEMENT FOR THE ELECTRO-OPTICAL CONTROL AND FAST MODULATION OF THZ TRANSMITTERS AND THZ MEASURING SYSTEMS

The invention pertains to an arrangement for the electro-optical control and fast modulation of THz transmitters and THz measuring systems, with this arrangement featuring at least two single mode semiconductor lasers with a relative wavelength difference in order to generate beat signals with the desired THz frequency, wherein at least one of said semiconductor lasers can be electrically tuned with respect to the wavelength, with the arrangement also featuring means for superimposing both laser waves and for generating superimposed beat signals at two outputs, wherein one beat signal at one output serves for controlling a THz transmitter and another beat signal at the other output serves for controlling a local oscillator in the THz receiver, and with the arrangement furthermore featuring at least one means for adjusting the relative phase correlation of the beat signals at the respective outputs for the THz transmitter and the local oscillator.

Arrangements of this type are used in the electromagnetic radiation range between 0.3 THz and 10 THz, i.e., in the so-called terahertz range, e.g., in safety engineering, analytics or spectroscopy. In this case, tunable transmitters and sensitive detection techniques represent a bottleneck. The above-described control is intended to make it possible to use homodyne measuring techniques for the sensitive detection of THz signals.

Electronic solutions reach their limits at these high frequencies and the low photon energy (lower than or near kT of the thermal radiation at room temperature) is problematic with respect to the optical generation (laser) and detection of the radiation. The intensive cooling required, e.g., in quantum cascade lasers and bolometer detectors results in costly and bulky THz systems.

An increasingly favored flexible and compact solution for terahertz measuring systems is described in International Journal of Infrared and Millimeter Waves, Vol. 26, No. 2, February 2005, pp. 201-207, particularly in FIG. 1. Two lasers with identical polarization, but different wavelength, are superimposed by utilizing a beam splitter. This creates a power beat signal with a frequency that correlates with the wavelength difference between the two lasers. The beat frequency can be very easily adjusted and, e.g., varied within the interesting THz range by choosing suitable laser wavelengths or by tuning the wavelength of one of the lasers. The power THz beat is optoelectrically converted in a following photomixer—e.g., an ultra-fast photoconductor—and the photocurrent signal produces charge carrier movements in an integrated antenna that ultimately emits THz radiation with the beat frequency.

A similar configuration on the receiving end serves for the sensitive homodyne detection of the THz radiation. In this case, the antenna receives the THz radiation. The optical beat signal of the second output is injected into the photomixer as local oscillator (LO). Consequently, a mixing product between THz wave and LO signal is produced in the photomixer and detected as quantity to be measured. The quantity of the mixing product depends on the intensity of the involved signals, but also on the phase correlation of the THz radiation relative to the local oscillator. This is the reason why the relative phase correlation is varied in small increments within a range greater than $\pi$ with the aid of the phase adjusting means and the quantity of the mixing product THz wave—LO is measured for the different phase correlations. The modulation amplitude of the mixing product is determined as a function of the phase variation and the determined value then serves as the measure for the power and phase of the THz radiation.

Such a complete series of measurements with a variation of the phase correlations is required in order to determine the power at any THz frequency and at any observed point. Consequently, the speed of the phase adjusting means decisively influences the measuring speed.

Until now, the phase variation was realized by means of a mechanically moved delay line in the mm-range according to the wavelength of the THz radiation.

However, phase modulations with mechanical delay lines have the following disadvantages:

The mechanism is slow such that the measuring speed is also very slow. This is unacceptable, in particular, when measuring a broad THz spectrum and in imaging scanning methods that require a high measuring speed in "Video Rate."

Slow also means that integration techniques for improving the signal-noise ratio cannot be used optimally. The sensitivity to weak signals is therefore limited.

Mechanical delay lines are voluminous and not very stable.
Fine-mechanical precision components are expensive.

The objective of the invention therefore is to disclose an inexpensive and compact arrangement for the electrical control and fast modulation of THz transmitters and THz measuring systems, wherein said arrangement is stable, requires no mechanical movements and operates with a purely electric control, consumes little power and also has a high speed potential for the phase modulation.

In an arrangement of the initially cited type, this objective is attained in that the at least one means for adjusting the phase correlation of the beat signals consists of an electrically controllable, semiconductor-based phase modulator for the spectral range of a laser wave, wherein said phase modulator is arranged in an individual light path between one of the lasers and the means for superimposing the two laser waves and able to electrically modulate the phase of the laser wave by at least $\pi$, and in that the two single mode semiconductor lasers are connected to the means for superimposing the two laser waves and for generating the superimposed beat signals at the two outputs, as well as to the phase modulator, by means of waveguides and compactly arranged on a chip with a stable phase.

According to the invention, the components known from the state of the art, namely the two lasers, the beam splitters, the couplers and the mechanically moved delay line, are replaced with a compact monolithic or hybrid integrated chip, particularly a so-called optical master chip without moving parts that features the above-described inventive means, such that the two generated beat signals are respectively delivered to different chip outputs in order to separately control the THz transmitter and the local oscillator.

The phase modulator in an individual light path of a laser wave changes the phase correlation between the two laser waves. This also influences the phase correlation of the beat signal and the subsequent THz wave. In a phase modulation of the beat signal and of the THz wave by $\pi$, it is important that the phase of the individual light wave is also modulated by $\pi$ because phase modulations of the optical beat signal are transmitted 1:1 to the THz wave that is generated, e.g., in the photomixer or antenna, respectively. Expressed in absolute values, a phase change $\pi$ of a light wave with a wavelength of, e.g., 1.5 μm corresponds to a change of the optical distance of approximately 0.75 μm, wherein the change of the optical distance for a THz wave lies between 100 μm and 1 mm. The latter distance changes and phase shifts can only be realized by means of optical delay lines with mechanical movements as they were also realized in arrangements known so far. The phase modulations of the laser wave by π in waveguides of the III-IV material system, in contrast, can be realized very easily and with high frequency by means of current or charge carrier injection or with an applied voltage or electric fields, respectively. Current modulations of mA or voltage modulations in the Volt range in phase sections with a length of approximately 100 µm consequently replace voluminous, relatively slow and less stable delay lines that are moved mechanically.

Another decisive aspect for attaining the objective of the invention is that the desired phase modulations are not disturbed by undesirable phase instabilities. For example, if individual lasers are connected to the phase modulator and the coupler by means of fibers, it can be expected that significant instabilities will occur—analogous to interferometers according to the fiber technology. It is therefore necessary to design a compact and robust system consisting of the two lasers, the phase modulator, the couplers and the optical waveguides, i.e., the components need to be integrated on a chip in a monolithic or hybrid fashion. This integrated chip needs to have two optical outputs in order to realize sensitive homodyne/heterodyne measuring techniques: one output for the signal of the laser beat with phase modulation and one output for the signal of the laser beat without phase modulation (local oscillator). In this case, the assignment of these two outputs is not important for the respective control of the transmitter and the receiver because only the relative phase correlation signal LO is important in the above-described detection techniques.

The flexibility of the inventive solution can be improved with the integrated arrangement of another phase modulator on the chip in the individual light path of the second laser, namely between the second laser and the coupler.

In the common beam path behind the couplers, phase instabilities practically affect both waves equally, i.e., they do not disturb the relative phase correlation. This advantageously makes it possible to utilize glass fibers for connecting the new optical master chip to the respective photomixers on the THz transmitter and the homodyne receiver.

The integration of the laser and the phase modulator is essential for the desired THz phase modulation. However, the entire remaining characteristic of the THz radiation can be electrically controlled relatively fast by implementing other functions. If one of the lasers is realized in the form of a tunable laser, the THz frequency can be varied accordingly. If an optical amplifier is integrated in front of the output to the transmitter, the power can be adjusted and also quickly modulated, e.g., for applications of the Lock-In technique—by means of an electric modulation of the amplification.

The optical master chip therefore makes it possible to adjust all parameters of the THz wave—frequency, phase correlation, amplitude—with a purely electric control and to quickly modulate these parameters. In addition, the chip also contains a local oscillator for reference signals that is required for sensitive homo/heterodyne detection techniques at the second output.

The arrangement also provides particular advantages when it is used in the Lock-In technique. This technique is used for improving the signal-noise ratio and for suppressing the influence of background radiation. At room temperature, THz radiation and thermal radiation lie in a similar energy range such that the Lock-In technique is essential in uncooled THz systems. The power of the THz transmitter is usually modulated with a suitable frequency, e.g., by means of a chopper in the optical beam path. The mixing product in the receiver is then measured over an appropriate integration time in a frequency-selective and phase-selective fashion (referred to the above-described modulation) with a Lock-In amplifier.

Instead of modulating the power of the THz transmitter, the inventive arrangement also makes it possible to adapt the phase correlation of the THz radiation with very high frequency, e.g., to the Lock-In frequency, and to exactly modulate the phase correlation by π.

In this case, the signal measured by means of Lock-In directly results in the modulation amplitude of the mixing product, i.e., the quantity that is directly correlated with the sought-after power of the THz radiation. In the inventive solution, the Lock-In technique and the variation of the phase correlation THz wave—LO are realized simultaneously and in one step such that the measuring and evaluation process is additionally accelerated and the significant measured value can be displayed directly.

It is proposed that the active components of the chip consist of the material system III-IV, preferably InGaAsP or GaAlAs, and that the chip is integrated in one of the aforementioned material systems in a monolithic fashion. However, the chip may also be integrated in a hybrid fashion on a Si platform or polymer platform.

The above-described embodiments, as well as other embodiments, are defined in the dependent claims.

Embodiments of the invention are described in greater detail below with reference to the drawings.

In these drawings.

Figure 1:
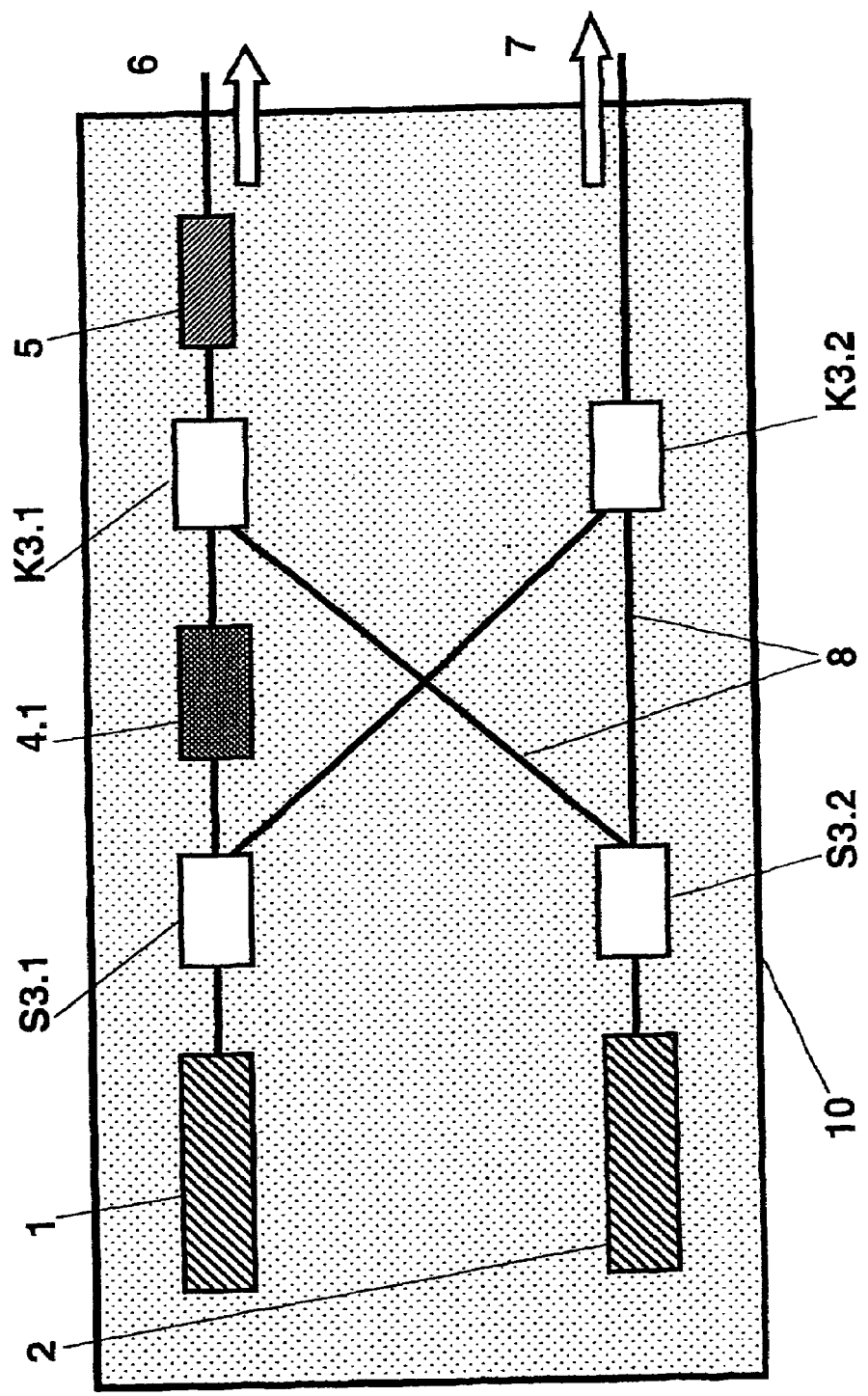
FIG. 1 shows an embodiment of the invention with a phase modulator, in which the lasers emit on one side.

In the first embodiment that is schematically illustrated in FIG. 1, an optical master chip 10 according to the invention features two single mode semiconductor lasers 1, 2 that emit laser waves of different wavelengths on one side, wherein these laser waves are respectively split in a beam splitter S3.1, S3.2. A phase modulator 4.1 is used for modulating the phase correlation of one part of the laser wave of the laser 1, wherein the non-modulated part of the laser wave of the laser 2 is subsequently superimposed on the aforementioned part in the coupler K3.1 and delivered to the output 6. The two other non-modulated parts of the laser waves of the lasers 1, 2 are superimposed in the coupler K3.2 and delivered to the other output 7. This means that the parts of the two laser waves of the lasers 1, 2 are superimposed once without phase modulation and superimposed once with phase modulation and then delivered to the different chip outputs 6, 7 for the separate control of the THz transmitter and the local oscillator. The relative phase correlation of the beat signals consequently can be varied in small increments within a range greater than π by means of the phase modulator 4.1. An amplitude modulator 5 is arranged between the coupler K3.1 and the output 6 in order to adjust and also quickly modulate—by means of an electric modulation of the amplification—the power of the beat signal in this path.

Figure 2:
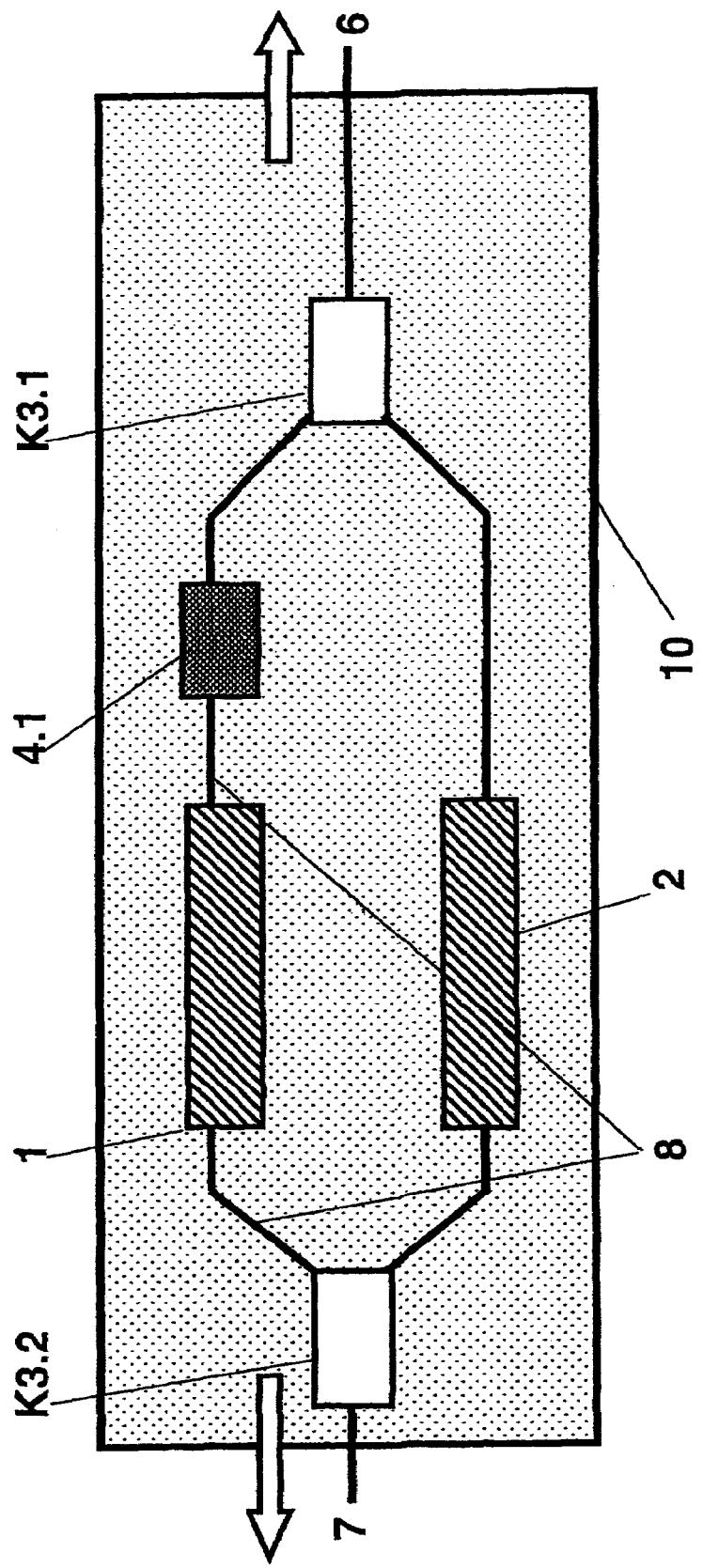
FIG. 2 shows another embodiment of the invention with a phase modulator, in which the lasers emit on two sides.

In the embodiment that is schematically illustrated in FIG. 2, both lasers 1, 2 emit in two directions such that two partial beams are already present per laser 1, 2 wherein the phase modulator 4.1 is once again arranged in front of the coupler K3.1 in the light path of a partial beam of the laser 1. The partial beams are also superimposed as described above in this case.

Figure 3:
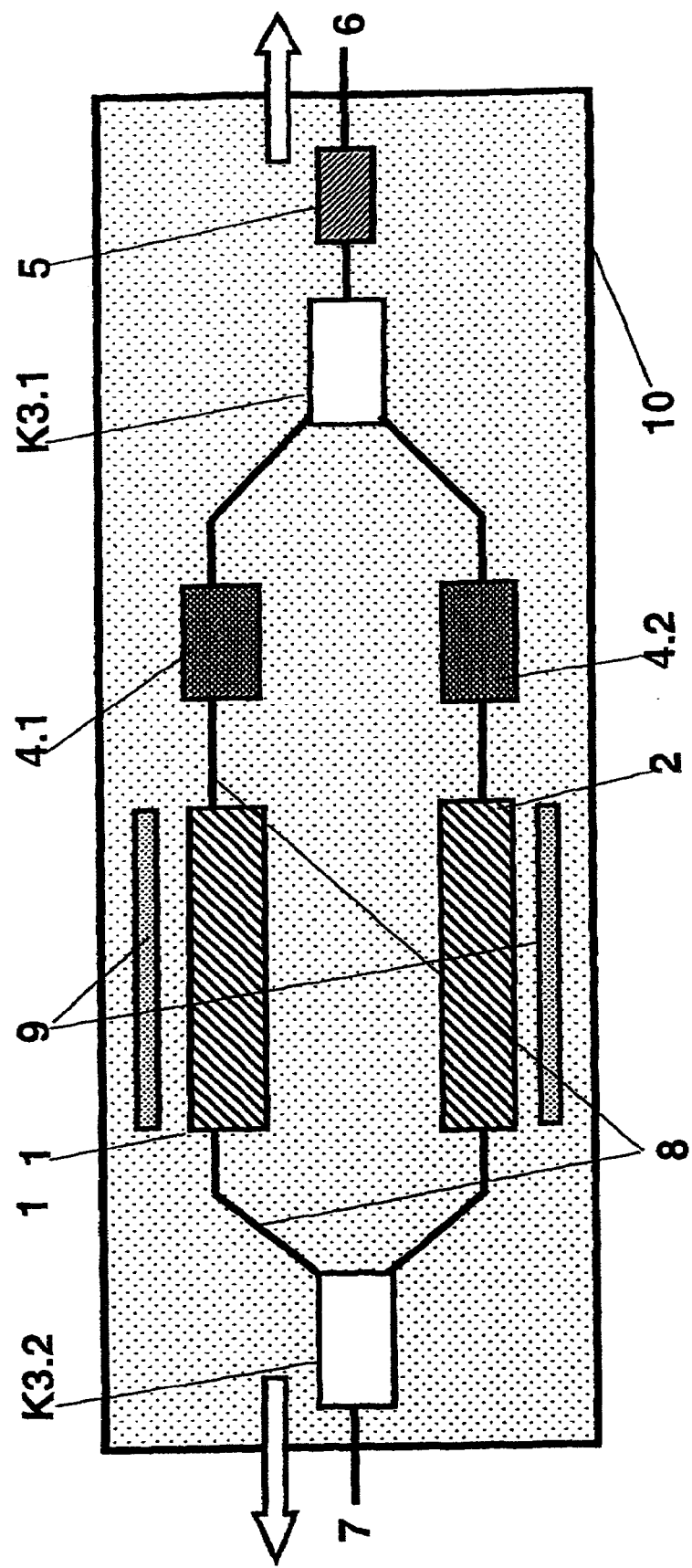
FIG. 3 shows another embodiment according to FIG. 2 with another phase modulator.

In comparison with the preceding embodiment, the embodiment illustrated in FIG. 3 features an additional phase modulator 4.2 that is arranged in the individual light path of the second laser 2, namely between this laser and the coupler K3.1. The two lasers 1, 2 can be thermally tuned and feature heating means 9. In this embodiment, an amplitude modulator 5 is also arranged between the coupler K3.1 and the output 6 in order to adjust the power of the beat signal.

The invention claimed is:

1. An arrangement for the electro-optical control and fast modulation of THz transmitters and THz measuring systems, with this arrangement featuring at least two single mode semiconductor lasers with a relative wavelength difference in order to generate beat signals with the desired THz frequency, wherein at least one of said semiconductor lasers can be electrically tuned with respect to the wavelength, with the arrangement also featuring means for superimposing both laser waves and for generating superimposed beat signals at two outputs, wherein one beat signal at one output serves for controlling a THz transmitter and another beat signal at the other output serves for controlling a local oscillator in the THz receiver, and with the arrangement furthermore featuring at least one means for adjusting the relative phase correlation of the beat signals at the respective outputs for the THz transmitter and the local oscillator,
characterized in that
the at least one means for adjusting the phase correlation of the beat signals consists of an electrically controllable, semiconductor-based phase modulator (4.1) for the spectral range of a laser wave, wherein said phase modulator is arranged in an individual light path between one of the lasers (1 or 2) and the means (K3.1 or K3.2) for superimposing the two laser waves and able to electrically modulate the phase of the laser wave by at least $\pi$, and in that
the two single mode semiconductor lasers (1, 2) are connected to the means for superimposing the two laser waves (K3.1, K3.2) and for generating the superimposed beat signals at the two outputs (6, 7), as well as to the phase modulator (4.1), by means of waveguides (8) and compactly arranged on a chip (10) with a stable phase.

2. The arrangement according to claim 1,
characterized in that
the waveguides (8) are arranged in such a way that the two laser waves that are respectively emitted from one side of the two lasers (1, 2) are split into two parts by means of beam splitters (S3.1, S3.2) and a partial beam of the first laser (1) is, after it passes through the modulator (4.1), superimposed on a partial beam of the second laser (2) by means of a coupler (K3.1) and delivered to the output (6), and in that the other two partial beams that do not pass through the phase modulator (4.1) are superimposed by means of a coupler (K3.2) and delivered to the other output (7).

3. The arrangement according to claim 1,
characterized in that
the waveguides (8) are arranged in such a way that both laser waves emitted from both sides of the two lasers (1, 2) are used, wherein the laser waves emitted from one side of the two lasers (1, 2) are superimposed with the laser wave of the second laser (2) by means of a coupler (K3.1) after the laser wave of the first laser (1) passes through the phase modulator (4.1) and delivered to the output (6), and in that the laser waves emitted from the other side of the two lasers (1, 2) are superimposed by means of a coupler (K3.2) and delivered to the other output (7).

4. The arrangement according to claim 1,
characterized in that
another phase modulator (4.2) is arranged in the individual light path of the second laser (2), namely between the laser (2) and the coupler (K3.2 respectively K3.1), and integrated on the chip (10).

5. The arrangement according to claim 1,
characterized in that
an electrically controllable amplitude modulator (5) is arranged between one of the couplers (K3.1 or K3.2) and the adjacent output (6 or 7) and integrated on the chip (10).

6. The arrangement according to claim 1,
characterized in that
the second semiconductor laser (2) can also be electrically tuned with respect to the wavelength.

7. The arrangement according to claim 1,
characterized in that
the lasers consist of lasers that can be tuned in a purely electronic fashion.

8. The arrangement according to claim 7,
characterized in that
the lasers that can be tuned in a purely electronic fashion consist of DBR lasers.

9. The arrangement according to claim 1,
characterized in that
the lasers can be thermally tuned.

10. The arrangement according to claim 1,
characterized in that
the phase modulator (4.1; 4.2) is based on a refractive index change due to charge carrier injection.

11. The arrangement according to claim 1,
characterized in that
the phase modulator (4.1; 4.2) is based on a refractive index change due to applied electric fields.

12. The arrangement according to claim 1,
characterized in that
the phase modulator (4.1; 4.2) can be modulated by $\pi$ with high frequency.

13. The arrangement according to claim 5,
characterized in that
the amplitude modulator (5) consists of a semiconductor amplifier, the amplification of which can be electrically varied and modulated.

14. The arrangement according to claim 1,
characterized in that
the active components (1, 2, 4.1, 4.2, 5) of the chip (10) are based on the material system III-IV, preferably InGaAsP or GaAlAs.

15. The arrangement according to claim 14,
characterized in that
the chip (10) is integrated in a monolithic fashion in the material system InGaAsP or GaAlAs.

16. The arrangement according to claim 1,
characterized in that
the chip (10) is integrated in a hybrid fashion on a Si platform.

17. The arrangement according to claim 1,
characterized in that
the chip (10) is integrated in a hybrid fashion on a polymer platform.

18. The arrangement according to claim 1,
characterized in that
the outputs (6, 7) of the chip (10) are connected to glass fibers in order to couple and additionally guide the beat signals.

* * * * *